United States Patent [19]

Fuhr et al.

[11] Patent Number: 5,203,346
[45] Date of Patent: Apr. 20, 1993

[54] NON-INVASIVE METHOD FOR DETERMINING KINEMATIC MOVEMENT OF THE CERVICAL SPINE

[75] Inventors: Arlan W. Fuhr, Scottsdale, Ariz.; Jack Winters, Takoma Park, Md.; Paul J. Osterbauer, Phoenix, Ariz.

[73] Assignee: Whiplash Analysis, Inc., Phoenix, Ariz.

[21] Appl. No.: 739,913

[22] Filed: Aug. 2, 1991

Related U.S. Application Data

[63] Continuation-in-part of Ser. No. 503,050, Mar. 30, 1990, abandoned.

[51] Int. Cl.$^5$ ............................................. A61B 5/11
[52] U.S. Cl. ................................... 128/781; 128/782
[58] Field of Search .............................. 128/781, 782; 273/186.3, 186.4

[56] References Cited

U.S. PATENT DOCUMENTS

| | | |
|---|---|---|
| 3,699,856 | 10/1972 | Chabot et al. |
| 3,906,931 | 9/1975 | Terekhv |
| 3,955,562 | 5/1976 | Farrar, Jr. |
| 3,973,332 | 8/1976 | Slomski |
| 4,146,311 | 3/1979 | Murr |
| 4,182,316 | 1/1980 | Nilsson |
| 4,375,674 | 3/1983 | Thornton |
| 4,416,293 | 11/1983 | Anderson et al. |
| 4,528,990 | 7/1985 | Knowles |
| 4,586,515 | 5/1986 | Berger |
| 4,598,717 | 7/1986 | Pedotti |
| 4,600,012 | 7/1986 | Kohayakawa et al. |
| 4,600,016 | 7/1986 | Boyd et al. |
| 4,631,676 | 12/1986 | Pugh |
| 4,655,227 | 4/1987 | Gracovetsky |
| 4,664,130 | 5/1987 | Gracovetsky |
| 4,670,781 | 6/1987 | Aubert et al. |
| 4,699,156 | 10/1987 | Gracovetsky |
| 4,760,851 | 8/1988 | Fraser et al. |
| 4,777,965 | 10/1988 | Allison et al. |
| 4,779,629 | 10/1988 | West et al. |
| 4,813,436 | 3/1989 | Au |
| 4,971,069 | 11/1990 | Gracovetsky |

FOREIGN PATENT DOCUMENTS

| | | |
|---|---|---|
| 128390 | 12/1984 | European Pat. Off. |
| 310901 | 4/1989 | European Pat. Off. |
| 216624 | 12/1984 | German Democratic Rep. |
| WO87/00026 | 1/1987 | PCT Int'l Appl. |
| 219075 | 12/1968 | U.S.S.R. |
| 427697 | 6/1969 | U.S.S.R. |
| 904666 | 2/1982 | U.S.S.R. |
| 1210783 | 2/1986 | U.S.S.R. |

OTHER PUBLICATIONS

Chao et al. "Measurement of Neck Range and Pattern of Movement." Abstract #319, XII Int'l. Cong. Biomech., UCLA, Los Angeles, CA 1989.

White et al. *Clinical Biomechanics of the Spine.* J. B. Lippincott Co., 2nd ed. pp. 92–115.

Winters et al. "Neck Muscle Activity and 3-D Head Kinematics During Quasi-Static and Dynamic Tracking Movements." Ch. 28. *Multiple Muscle Systems.* Winters and Woo, editors. Springer-Verlag, New York. 1990.

Peles et al. "Organization of Neck Muscle Activity for Quasi-Static and Dynamic 3-D Head Movements." First World Congress of Biomechanics-San Diego, CA. 1990. p. 208.

Winters et al. "Relations Between Neck Muscle Activity and Screw Axis Parameters of the Head." First World Congress of Biomechanics-Abstracts, vol. II. University of Ca., San Diego, CA 1990. p. 209.

(List continued on next page.)

*Primary Examiner*—Lee S. Cohen
*Assistant Examiner*—Kevin Pontius
*Attorney, Agent, or Firm*—Leydig, Voit & Mayer

[57] ABSTRACT

A non-invasive method for determining kinematic movement of the cervical spine. The method compares biomechanical pathways of a human patient's head free range of motion in space with either standardized biomechanical pathway data or previously determined biomechanical pathway data of the same person to determine the nature and extent of abnormal kinematic movement.

2 Claims, 5 Drawing Sheets

OTHER PUBLICATIONS

Peles. "Relations Between Neck Muscle Activity and Three-Dimensional Head Kinematics During Natural Head Tracking Movements." M. S. Thesis. Arizona State University. 1990.

Brugger et al., Computer-Aided Tracking of Body Motions Using A C.C.D.-Image Sensor, Med. & Biol. Eng. & Comput., 1978 vol. 16, No. 2, 207–210.

Gilman et al., "Measurement of Head Movement During Auditory Localization," Behavior Research Methods & Instrumentation, 1979, vol. 11(1), 37–41 (FIGS. 2, 3 & 5).

Grew, et al., "A Method of Measuring Human Body Shape & Movement-The Vector Stereograph," Engineering in Medicine, 1979, vol. 8, No. 3, 115–118.

Huntington et al, "A Method of Measuring from Photographic Records the Movements of the Knee Joint During Walking", Engineering in Medicine, '79 vol. 8, #3 (FIGS. 2 & 5).

Kasvand, et al, "Computer & The Kenesiology of Gait," Comput. Biol. Med., 1976, vol. 6, No. 2, 111–120 (see FIGS. 1–5).

Leo, et al., "An Optoelectronic Device-Microcomputer Sys. for Automated Gait Analysis Changes in Health Care Instrument." Due to Microprocessor Technology, '81 (see FIG. 4).

Panjabi et al., "A Technique for Measurement & Description of Three-Dimensional Six Degree-Of-Freedon Motion of a Body Joint With An Application to the Human Spine," J. Biomechanics, 1981, vol. 14, No. 7, 447–460.

Wyss et al., "Kinematic Data Acquisition System for Two-or Three-Dimensional Motion Analysis", Med. & Biol. Eng. & Comput. 1981, vol. 19, No. 2, 287–290.

NON-INVASIVE METHOD FOR DETERMINING KINEMATIC MOVEMENT OF THE CERVICAL SPINE

CROSS-REFERENCE TO RELATED APPLICATION

This application is a continuation-in-part of U.S. Pat. application Ser. No. 07/503,050, filed Mar. 30, 1990, now abandoned, and entitled "Non-Invasive Method for Determining Kinematic Movement of the Cervical Spine."

FIELD OF THE INVENTION

The present invention relates generally to a non-invasive method for determining the kinematic function of the cervical spine. More particularly, the invention relates to a non-invasive method for determining a patient's three-dimensional (3-D) head axis of rotation during specific movements. The head axis of rotation is subsequently used in conjunction with normal data bases for diagnosis of abnormal kinematic function of the cervical spine due to injury and to monitor therapy administered for the treatment of neck injuries.

BACKGROUND OF THE INVENTION

Over the years there has been considerable effort to formulate reliable methods and apparatus for measuring the movement of human body parts. Measurements of movement are made to determine if they fall within normal ranges of motion and to provide comparative information for future reference to monitor changes. For many movements, complete definition of a range of motion requires 3-D measurement. Spinal motion is a typical example. The kinematic function of the cervical spine has received considerable attention in recent years because of a large number of people who suffer from back pain.

Abnormal kinematic function of the cervical spine due to cervical sprain or cervical strain injuries resulting from, for example, automobile accidents, which are commonly known as "whiplash injuries," afflict over 1,000,000 Americans annually. Such injuries typically involve soft tissue damage only, and a major medical as well as legal problem is to determine not only the extent of injury at the outset, but also to determine the effects of therapy and medical treatment. Various methods of x-ray analysis (an invasive method) of the head and neck have been proposed. Only skeletal damage and major soft tissue changes can be seen with invasive techniques, and then only in the most severe cases. Computerized Tomography (CT) and Magnetic Resonance Imaging (MRI) studies have similarly been made, but they have failed to provide non-invasive, diagnostic or prognostic parameters to use as a predictor of the clinical condition.

Presently, head range of motion is the accepted non-invasive method for clinical evaluation of neck injuries. This technique, however, does not provide information concerning the exact kinematic function of the cervical spine during head movements. Furthermore, the results of such examinations can easily be swayed by conscious actions of the patient. This invention provides a non-invasive clinical tool for the assessment of neck function that does not suffer from these drawbacks.

The theory of this invention is based on the fact that the head is the final link in an open kinematic chain that includes the neck. Therefore, head movements are the final product of relative rotation about the cervical and upper thoracic vertebral joints with individual contributions depending on active muscle contraction and passive constraints (i.e., ligaments, intervertebral discs and facet orientations). Kinematic redundancy in this system is prevalent. For example, it is possible to produce mid-range, flexion-extension movements by concentrating the vertebral rotation about the upper cervical spine, the lower cervical spine or by distributing the rotation throughout the neck. Because the head is serially linked with the neck, such changes in cervical kinematics will be reflected by corresponding changes in head kinematics. (Chao, E.Y.S., Tanaka S., Korinek and Cahalan, T. (1989) Measurement of neck range and pattern of movement, Abstract 319, XII Int. Congr. Biomech., UCLA, Los. Angeles.). Variations in neck kinematics can be brought forth by injury to soft tissues in certain neck regions (e.g., injury to the upper cervical spine could necessitate rotation about the lower cervical spine). Therefore, head kinematics can provide a "window" to neck function/dysfunction. The kinematics of choice pertain to the head 3-D axis of rotation during specified movements.

The axis of rotation can be described in its finite or instantaneous form. The finite axis of rotation is the directed line in space about which the head rotates during a finite displacement (e.g., head rotation from 0° to 10°). The instantaneous axis is the limiting case of vanishing displacement and, therefore, yields a complete description of cervical function during head movements. Both of these axes can be defined by the screw axis parameters, which include the axis planar crossing (x,y,z coordinates), the axis direction vectors (x,y,z unit vectors), the rotation angle and the sliding component. The axis crossing and direction vector parameters are especially powerful in determining cervical function. For instance, during head extension movements, the crossing vectors correspond to the position of the axis on the mid-sagittal plane, thus giving a measure of cervical level of rotation. The direction vectors then characterize the degree of coupled motion inherent within the movement, thereby providing information concerning asymmetric neck kinematics.

Through experimental testing it has been established that uninjured subjects have constant and similar screw axis patterns during natural head movements and that injured patients tend to alter these patterns in response to their injuries. This allows the present invention to determine the existence and region of neck injury by noting differences in neck kinematic function between patients and normal data bases via the screw axis parameters.

The finite and instantaneous axis of rotation of a rigid body can be found by a variety of mathematical techniques. The finite planar axis can be found by methods such as the classical Rouleaux method (e.g., Panjabi, M. M., "Centers and Angles of Rotation of Body Joints: A Study of Errors and Optimization," *J. Biomechanics*, 12:911-920 (1979)) or the rotation matrix method of Spiegelman and Woo, S., "A Rigid-Body Method for Finding Centers of Rotation and Angular Displacements of Planar Joint Motion," *J. Biomechanics*, 20:715-721 (1985)). These planar aces are a subset of the more general 3-D screw axis analysis but do not provide the 3-D screw axis parameters for the head-neck system.

The 3-D axis for a given finite rotation can be obtained by two mathematically distinct methods, which take advantage of the x,y, and z coordinates of markers attached to the rigid body: i) analysis based on the displacement matrix approach (e.g., Suh, C. H. and Radcliffe, C. W. *Kinematics and Mechanisms Design*, John Wiley & Sons, N.Y., 1979); and ii) an approach based on minimizing error in the matrix formulation (Spoor, C. W. and Veldpau, F. E. "Rigid body motion calculated from spatial co-ordinates of markers, "*J. Biomechanics*, 13:391-393 (1980); Woltring, H. J., Huiskes, R., De Lange, A. and Veldpaus, F. E. "Finite centroid and helical axis estimation from noisy landmark measurements in the study of human joint kinematics, " *J. Biomechanics*, 18:379-389 (1985)). In the first case, the algorithm uses each combination of a 4 markers to estimate the screw axis parameters. Thus, with 5 markers, there are 5 solutions that, in theory, are the same and, with 6 markers, there are 15 such solutions. The best estimate is then either the average or the median of the population. The second method utilizes all markers to estimate the appropriate information, essentially numerically solving an optimization problem. Past results suggest that the latter method is superior. Woltring, H. J., Huiskes, R., De Lange, A. and Veldpaus, F. E. "Finite centroid and helical axis estimation from noisy landmark measurements in this study of human joint kinematic, " *J. Biomechanics*, 18:379-389 (1985).

This powerful method for determining neck kinematic function via the screw axis parameters of the head, however, has not been used in past investigations. Engineering research on the cervical spine has resulted in a data base in which the basic parameters of cervical range of motion and static relationships of a vertebra to its adjacent vertebrae have been established to a first approximation. A limited amount of data exists in which the planar finite axis (e.g., centrode) has been found for individual vertebral rotations. Clinical Biomechanics of the Spine, White, A. A. and Panjabi, M. M., Second Edition, 1990, J. B. Lippincott, Phila., PA. These two-dimensional methods utilize cadavers or crude invasive techniques (e.g., X-rays) and, furthermore, do not give a measure of overall kinematic cervical function during head movements.

Models of whiplash injury have recently been attempted using both anthropomorphic dummies and computer simulation (reviewed by Winters (1978), Sances et al. (1981)). However, these studies have considered only the general relationship between possible injury modes and crash conditions. Also, the identifying parameters are typically head acceleration and head range of motion in rotation and translation. Screw axis parameters have not been of importance. Few measurements have been made on humans. More importantly, there is little relation between measurement of the kinematics of collision using models and measurement of voluntary movements in humans. None of these "whiplash injury" studies has ever used 3-D kinematic screw axis parameters of the head as a diagnostic tool to determine the extent of abnormal kinematic cervical spine movement. See Winters, J. Biomechanics; Wyss and Pollack, 1981, Med. Biol. Eng. Computers; Panjabi et al., J. Biomech. 14, 1981. Thus, actual non-invasive measurements of the instantaneous or finite axis of rotation have not been used or suggested for use as a predictor or diagnostic parameter of the basic biomechanical lesion produced by the whiplash injury.

U.S. Pat. Nos. 4,664,130 and 4,669,156 to Gracovetsky disclose a non-invasive method and equipment for the detection of a mechanical abnormality or injury in the lumbar or cervical spine of a patient and to identify this abnormality or injury as either of the compression or torsion type. In a first step, any variation of the lumbar curve of the patient is measured using a non-invasive technique. Then any discrepancy or asymmetry is detected in said measured variation of lumbar curve. Gracovetsky does not find the 3-D screw axis parameters of a specific rigid body (e.g., vertebrae or head), and, in fact, cannot obtain the 3-D axis using the method and equipment disclosed therein.

U.S. Pat. No. 4,528,990 to Knowels discloses a head-mounted apparatus for measuring the movement of the spine or head about a substantially vertical axis and is also capable of indicating spine or head tilting. A head-band firmly affixed to the head includes an indicia scale used in conjunction with a body reference indicator, whereby the indicator is maintained stationary while the spine or head is rotated such that the relationship between the indicator and indicia scale represents rotative body movement. A gravity-operated gauge is also affixed to the head with respect to the horizontal. This device only measures orientation (angular tilt) and there is no attempt to measure axis of rotation. The same applies to Farrar, U.S. Pat. No. 3,955,562 (1976).

Gilman et al. Instrumentation & Techniques, Measurement of Head Movement During Auditory Localization, Behavior Research Methods & Instrumentation, Vol. II(1), 37-41 (1979), uses a helmet apparatus with one light source marker to determine the angular position and velocity of the head in response to audio signals. The method, however, does not attempt and, in fact, cannot find the 3-D instantaneous or finite head axis of rotation. Even though Gilman et al. discloses that a 3-D system is contemplated, this addition would only allow for the determination of angular position in three axes and would still not provide axis of rotation data.

Gorron et al. discusses the use of x-rays to calculate the instantaneous axis of rotation of the cervical vertebrae, and claims to show that a change from normal occurred in a person's centerline, indicating a dislocation of the C-7 vertebrae. Gorron, J. P., Deschamps, G., Dimnet, J., Fischer, L. P., Kinematic Study of the Inferin Cervical Spine in Saggital Plane, pp. 32-37. In: P. Kehn & W. Widner (eds.) Cervical Spine I Springer-Verlag, N.Y. (1987). This method, however, does not and is not set up to calculate the 3-D screw axis parameters of the head to provide a measure of overall cervical function.

Huntington et al., A Method of Measuring from Photographic Records the Movements of the Knee Joint During Walking, IMechE, Vol. 8, No. 3 (1979), relates to a non-invasive diagnostic method and apparatus for determining real-time patient ranges of motion of the knee joint by utilizing at least one video camera to track and record light reflected from markers attached to the knee joint. Huntington et al. do not disclose the use of screw axis parameters and, furthermore, do not disclose a method or apparatus for use with the head-neck system.

Similar apparatus and methods have been used for study of the jaw, the back and the arm. For example, simple photography has been used to record jaw movement, and plots of the trajectory of jaw movement have been attempted. However, criteria for differentiating normal from abnormal movement have not been used, and the method is not applicable to the head-neck system.

Russian Patent No. 904,666 discloses a device that records an observer's head position while observing an object. A screen is placed on the head of the observer and carries a two point source of light. The measuring element of the point coordinates determines the Cartesian coordinates and transmits two X,Y values to a converter, which describes the movement of the two points and hence the movement of the head. By increasing the number of screens and recorders, the general case with three dimensions can be handled. There is no teaching to obtain screw parameters or to utilize such information as a diagnostic tool.

Berger, U.S. Pat. No. 4,586,515, discloses a device and method for measuring the position and/or motion of a body part, and, particularly, the head to diagnose spinal disorders. Three sensors are used to detect 3-D motion of the head. Rotation, flexion and lateral tilting of the head are detected by the device to determine the motion pattern of the body part in space to diagnose a motion disorder. Berger does not use biochemical screw axis pathways to determine the nature and extent of abnormal head movement.

Thus, despite the various attempts of those skilled in the art, the art has failed to develop a reliable method for determining abnormal kinematic movement of the cervical spine. More particularly, the art has failed to recognize the use of the 3-D kinematic screw axis parameters of the head as an indicator of cervical spine function and, thus, has failed to provide a satisfactory non-invasive method for using the 3-D kinematic screw axis parameters of the head as a diagnostic tool to determine the nature and extent of abnormal kinematic cervical spine movement.

Accordingly, it is a principal object of the present invention to provide a method for using finite and instantaneous 3-D kinematic screw axis parameters as a diagnostic tool to determine the nature and extent of abnormal kinematic cervical spine movement.

It is a more specific object of this invention to provide biomechanical, numerical parameters by which to establish abnormal kinematic function of the cervical spine, which occurs in patients who suffer "whiplash injury."

Yet another object of the invention is to provide a procedure necessary to carry out the above-identified methods.

These and other advantages of the invention as well as additional inventive features will become apparent from the following detailed description of a preferred exemplified embodiment of the invention and accompanying drawings.

SUMMARY OF THE INVENTION

The present invention is predicated on the discovery that the kinematic movement of a body part provides biologically relevant information about the pathway through which the body part rotates. The biomechanical pathway, in turn, provides a means by which to compare physically impaired movement with normal or standard movement for the diagnosis and prognosis of physical injury to the body part. The present invention is particularly useful with the head-neck system. The instantaneous axis of rotation vector, centrode and/or finite rotation pole of the head define the biomechanically relevant pathway of the head's movement. Because the head is the most distant member of the kinematic chain of the head-neck system, the biomechanical pathway of the head may be used to diagnose kinematic abnormalities in the cervical spine.

The present invention provides a non-invasive 3-D method for detecting the kinematic function of the cervical spine of a patient and can be used to detect abnormal kinematic functions as well. By the method of the present invention, the axis of rotation of the head is used to determine neck function by finding the cervical level of this rotation and any coupled motion.

The method of this invention includes positioning onto the head of a patient a marker means, which can be detected by a recording means as the patient's head moves through certain prescribed movements. A target or instruction means provides specific head movement patterns that can be followed by the subject via visual feedback supplied by a pointer means attached to the head. During head movements, the recording means detects the position of the marker means. The marker data are then processed by a 3-D analysis means to provide the 3-D coordinates of the markers. The 3-D coordinates of the markers are used by a mathematical rigid body program means to determine the finite and/or instantaneous screw axis parameters. The derived screw axis parameters that occur during the given task performed by the patient are then compared either (i) with screw axis parameters of predetermined standardized data to ascertain any discrepancy or (ii) with previously derived screw axis parameters for said patient to identify therapeutic changes.

DETAILED DESCRIPTION OF THE PREFERRED EMBODIMENT

While the invention will be described in connection with certain preferred embodiments and procedures, the present invention is not intended to be limited to those particular embodiments. To the contrary, the present invention is intended to cover all alternatives, modifications and equivalent arrangements as may be included within the spirit and scope of the invention as defined by the appended claims.

In accordance with the present invention, kinematic function of the cervical spine is detected by recording means, which record the patient's 3-D movements. The recording means record a signal from marker means, which are radially disposed about the head of the patient as the patient moves according to the target means. The target means is comprised of a combination of horizontal, vertical and oblique lines with landmarks indicating specific angles. The patient is instructed to follow the lines in a smooth motion for instantaneous or finite screw axis of rotation calculation and/or in a tracking pattern stopping at each landmark for the finite axis over specific angle increments. In so doing, the patient moves his head in the selected pattern and his head moves in three dimensions in space. As the patient follows the target patterns, his head's movement is recorded by recording means, which detect and record the movement of the marker means. With the use of a 3-D spatial analysis system, the 3-D coordinates of each of the marker means is determined. Using rigid body kinematic principles, kinematic parameters defining the "screw axis" about which the head is rotated are obtained. The derived screw axis parameter data for the patient may then be compared to standardized screw axis parameter data to determine the kinematic functions of the patient's cervical spine.

While the inventors do not wish to be bound to any particular theory, it is believed that an analysis of the last rigid body of the head-neck system, namely the head, will provide information that will be indicative of the kinematic function of the cervical spine. That theory is predicated on the fact that the head is at the end of a kinematic chain of rigid bodies that are intricately coupled, so that details of a given head orientation will depend on cervical spine function. For example, if the C1–C2 region cannot rotate normally, the screw axis of the head will be lower. Conversely, injury limiting the range of motion in the C5–C7 area will likely cause the axis to be higher for a given type of task.

The present invention provides a fully 3-D, quantitative analysis of the head-neck system by evaluating the cervical biomechanical pathway of the head during natural head movements. Deviations in the biomechanical pathway of the person under test from standardized data, or normal, are indicative of abnormal movement of the cervical spine and, in turn, indicate injury to the spine. Thus, by observing the biomechanical pathway of the patient under test, asymmetries anywhere in the cervical spine can be immediately identified. Moreover, because of wide variability in the screw axis vector directions, more abnormalities may be measured using the method of the present invention as compared to any prior means. For example, movements such as axial rotation and lateral flexion are, in fact, often more difficult for individuals with whiplash injuries, which typically involve soft tissue damage. Subtle changes in the screw axis parameters of individuals with whiplash injury are measurable in accordance with the present invention and can be used satisfactorily as clinical evaluators, without invasive methods and without knowledge of the pathomechanical cause of the injury.

Accordingly, of primary interest in the method of the present invention are the 3-D screw axis parameters for the head of a human patient. The screw axis parameters for the head consist of (a) the axis of rotation vector, (b) a point on this vector, and, as appropriate, (c) the angle of rotation about this vector and sliding along this vector and (d) the angular velocity. The biomechanical pathway of the head through its movement consists of the instantaneous axis of rotation, the centrode pathway, and the finite rotation pole. By calculating the biomechanical pathway, preferably with the aid of a computer, clinically reliable data can be obtained from which the degree of abnormal kinematic function can be ascertained. Desirably, the various elements of the biomechanical pathway are plotted graphically to facilitate comparison with the biomechanical pathways of standardized data, which may comprise, for example, the biomechanical pathways of a population of normal individuals, i.e., those who have not been injured, and/or with the patient's prior history. The method of the present invention thus provides a significant diagnostic and prognostic tool for determining the nature and extent of abnormal kinematic movement of the cervical spine.

Figure 1:
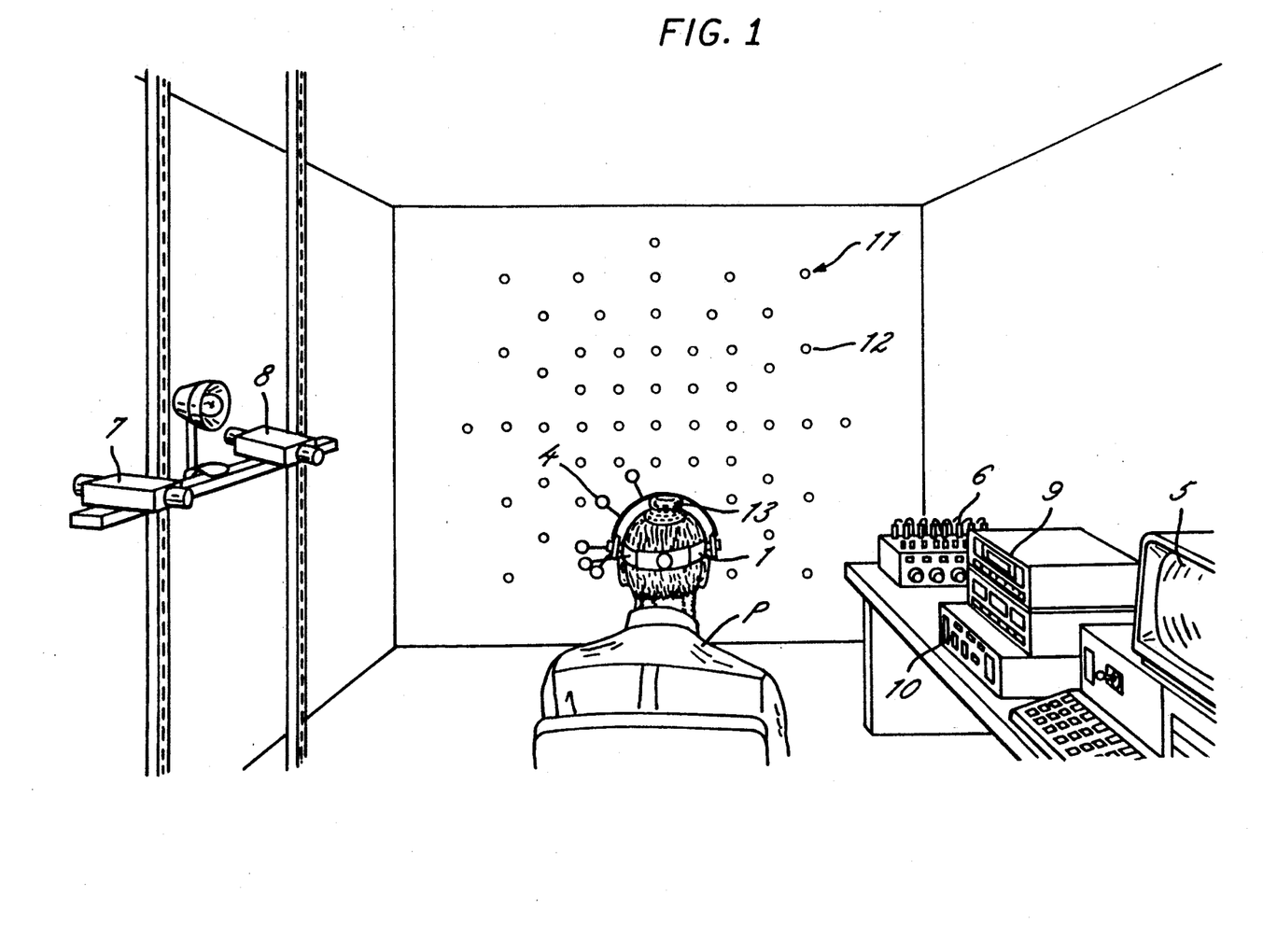
FIG. 1 is a perspective view of equipment suitable for carrying out the method of the present invention.

Turning to FIG. 1, there is shown equipment suitable for carrying out the method of the present invention. According to the illustrated embodiment, a helmet 1 is worn by the patient P. The helmet 1 can be adapted to various head sizes and shapes by means of an adjustable strap 2 (FIG. 2); and is preferably lightweight so that it can fit comfortably on the head. To carry out the testing (described in more detail hereinafter), the helmet is adjusted to fit snugly on the patient's head during the test. Thus, movement of the helmet will accurately reflect the patient's head movements.

Figure 2:
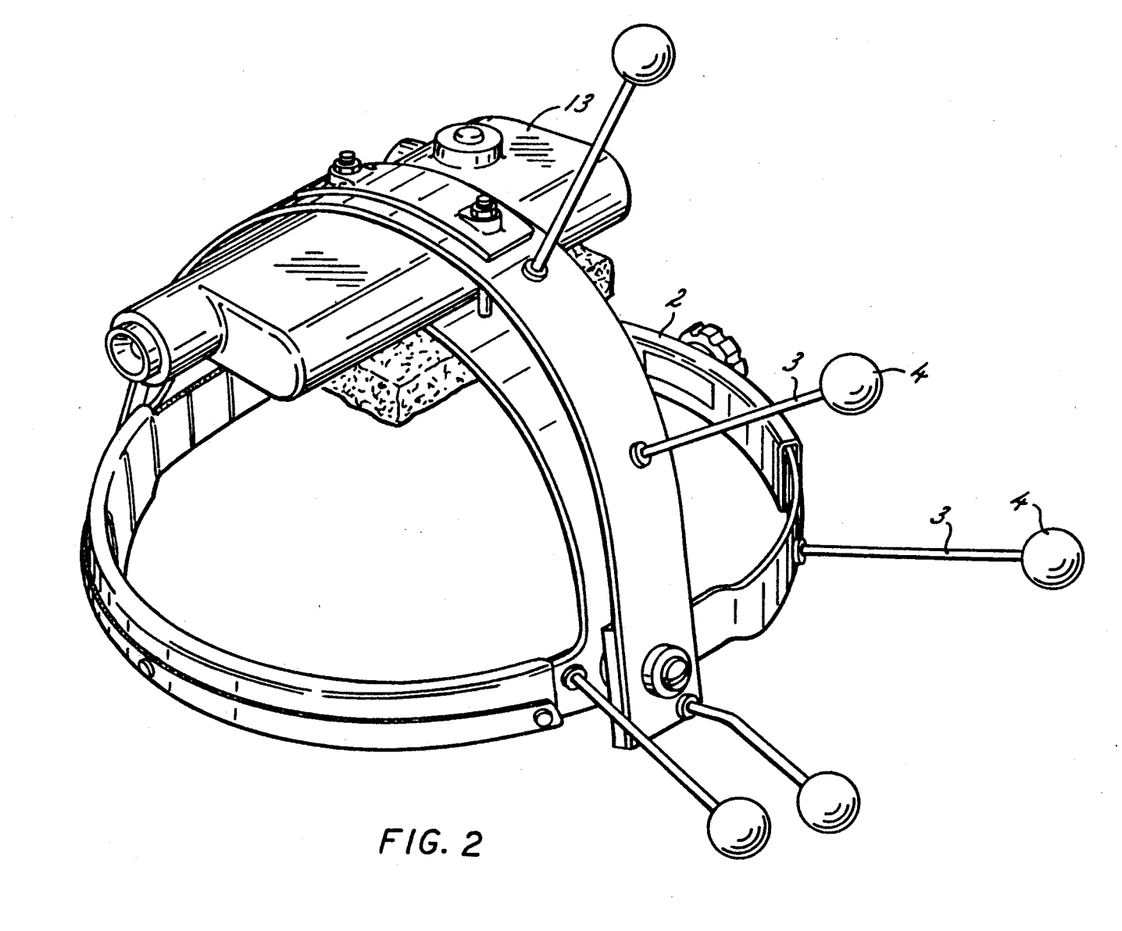
FIG. 2 is a perspective view of a helmet worn by the patient to provide the marker means and pointer means.

The helmet 1 includes marker means, which can be detected by a recording means to enable the determination of the patient's head orientation in space. The size and shape of the marker means is not critical to the method of the invention provided that the marker means are capable of being detected and recorded by the recording means. In the illustrative embodiment, the marker means comprise bolts 3 of variable length mounted to the helmet 1 and include on their ends a marker 4, which is capable of reflecting light. Preferably, the markers 4 comprise a one-half inch diameter spherical ball covered by a suitable reflective material, preferably retro-reflective tape. Preferably five or six bolts are mounted to the helmet in such a manner that all of the markers can be uniquely recorded by each recorder means without any marker overlap or marker interference, one with another, throughout the patient's range of motion.

The equipment for use in the present invention further includes a target means in preselected arrangement. The target means is comprised of a number of lines in a planar or dome-shaped fashion in horizontal, vertical and oblique orientations (FIG. 2). Landmark means, preferably circular, are placed at specific angle increments over the range. After verbal instructions, the patient tracks the target signal using visual feedback provided by the light source 13 and, in so doing, moves his head to follow the pattern that is created.

The target means, therefore, allows screw axis analysis for full 3-D head movements, including axial rotation (i.e., left to right movement), flexion-extension (i.e., up and down movement), oblique (X-shaped patterns) and box shaped patterns. The light source for indicating the tracking direction that the patient is to follow is preferably a lamp or a laser.

The preferred embodiment is a planar array of vertical, horizontal and oblique oriented lines placed on a wall with circular landmarks depicting specific angles. It will be appreciated that other types of target means may also be suitably employed. For example, active targets (e.g., lamps) can be electronically controlled to guide patients through movement patterns. The target pattern also can be placed on a partial sphere, allowing angle landmarks to be placed at equal distances apart and to provide more range of motion in less space.

In accordance with a preferred embodiment of the present invention, the indicator means 13 emits a beam of light, which is to be directed at the target to provide visual feedback for the patient.

In accordance with a preferred embodiment of the invention, the recording means comprise at least two standard CDC video cameras, 7 and 8, which record the position of the marker means throughout the preselected head motion tasks that the patient is asked to perform. The two cameras are placed relative to the patient's head so that all the markers 4 on the helmet 1 will be within the camera's recording view for the entire range of the patient's expected motion. Generally, the cameras are set at an angle of 50° to 60° relative to one another. However, the angle at which the cameras are located relative to one another is not critical provided they are not too close together, which may reduce accuracy, and provided that each camera can cover the entire range of expected motion and can continue to view all marker means and record their movement. In the preferred embodiment, the video recorders record light reflected by the marker means carried by the helmet, which corresponds to the patient's head movement in space.

Each video camera is connected to a video cassette recorder 9, 10, where a videotape of the patient's motion is recorded on videocassette. A monitor (not shown) may be used to view the video camera images as they are being recorded. In order to minimize unwanted reflecting artifacts from the video recording, it is preferred that all of the helmet elements other than the markers 4 be of a non-reflective color, such as dark blue or black.

In order to provide an accurate 3-D analysis of the patient's head movements, the two videotapes are first synchronized with an "Expert Vision Remote Site" unit, commercially available from Motion Analysis, Inc. The Expert Vision Remote Site unit synchronizes the camera sampling, which is done every 17 ms via a signal from the remote site to each camera, and places a user-initiated audio tone on each videotape at the same sampling frame. The remote site unit is connected to the VCR, which is hooked up to the two video cameras so that the timing marks are created simultaneously with the actual filming of the patient.

In accordance with the invention, the 3-D coordinates of the centroids of the markers 4 throughout the movement of the head during the patient's performance of the requested tracking tests are used to compute the finite rotation pole, the instantaneous axis of rotation and the centrode movement of the head. To obtain the 3-D coordinates of the centroid of each marker 4 from the videotape, the full "Expert Vision Motion Analysis System," commercially available from Motion Analysis, Inc., Santa Rosa, Ca., is preferably used. This system comprises a 3-D motion analysis system housed on a computer workstation and a master software program called "EV3d". While certain standard commands from the Expert Vision System are utilized for calibration and initialization, the special command "input" (in the Mev environment) is used to create computer files from videotape. The "input" command couples the computer to Motion Analysis "VP-110" hardware, or its equivalent, which measures the grey-level transition, which is essentially an outline of the markers 4, from a videotape. The "track" command of the Expert Vision System allows the computer files created from each videotape to be combined and the centroid or location for each marker throughout the head movement and in three-dimensions to be obtained for each motion task that the patient performs. Other photoelectronic, infrared or electromagnetic based systems may likewise be used.

After the marker locations have been determined, the screw axis parameters are calculated, preferably with the aid of a computer. To that end, software based on the equations first presented by Spoor, C. W. and Veldpaus, F. E., "Rigid body motion calculated from spatial coordinates of markers," *J. Biomechanics,* 13: 391–393 (1980) and as presented in Woltring, H. J., Huiskes, R., De Lange, A. and Veldpaus, F. E., "Finite centroid and helical axis estimation from noisy landmark measurements in the study of human joint kinematics," *J. Biomechanics,* 18: 379–389 (1985), the disclosures of which are incorporated herein by reference, may be used satisfactorily. Marker locations in addition to the four typically utilized by clinical, theoretical techniques are advantageously used to lower the error in the calculation due to measurement noise. Using the equations of Spoor and Veldpaus and Woltring, et al., the screw axis parameters or biomechanical pathway for the head, namely the instantaneous axis of rotation, a point on this axis (e.g., the finite rotation pole or centrode) and the rotation about and sliding along this axis can be obtained. Plots of these various movements and pathways may then be made by standard graphics methods.

Graphic plots of the derived screw axis parameters for the patient under test may then be used in either of two ways. The derived screw axis parameters may be used as a diagnostic tool, by comparing the screw axis parameters with standardized screw axis parameters, including, for example, plots of screw axis parameters for normally healthy persons, to ascertain any discrepancies between the two. In that way, any abnormal kinematic movement of the cervical spine can be observed and quantified so that the degree of injury can be established.

Therapeutic changes (e.g., improvement) in the kinematic function of the cervical spine also can be evaluated quantitatively by comparing the derived screw axis parameters of the patient after therapy to the analog of the screw axis parameters derived for that patient before therapy was begun. It will be readily apparent to those skilled in the art that the use of the derived screw axis parameters data after the injury combined with the screw axis parameters measured periodically after treatment will provide quantitative information regarding the patient's progress after therapy and the relative degree of impaired kinematic function from which the patient still suffers.

In order to carry out the method of the present invention, a patient P is fitted with the helmet 1 described above. The patient is then instructed to perform a series of voluntary range-of-motion tasks to provide the outside parameters of his range of motion for the actual test. More particularly, the patient starts by making standard, voluntary, self-paced, slow range-of-motion movement in the flexion-extension (up-down), axial rotation (left-right), and lateral bending (side-to-side) directions. Following the voluntary range-of-motion tasks, the patient is instructed to follow target patterns within his voluntary range of motion. Preferably five target patterns are used: left-right, up-down, a box pattern in either direction, and an oblique or x-shaped pattern. While the patient is following the target pattern, movement of the markers on the helmet (which correspond to head movement) are recorded on the synchronized videocassette tapes for further processing as described heretofore. The data recorded on the videotapes are then processed as described above. From that data, which correspond to the head's movements, the screw axis parameters are calculated and plotted. The derived plots are calculated and plotted. The derived plots are then compared to standard plots and/or to prior plots of the same patient so that the nature and/or extent of the abnormal kinematic movement of the cervical spine can be determined.

The following Examples are intended to further illustrate the invention described herein, and are not intended to limit the scope of the invention.

EXAMPLE I

Figure 3:
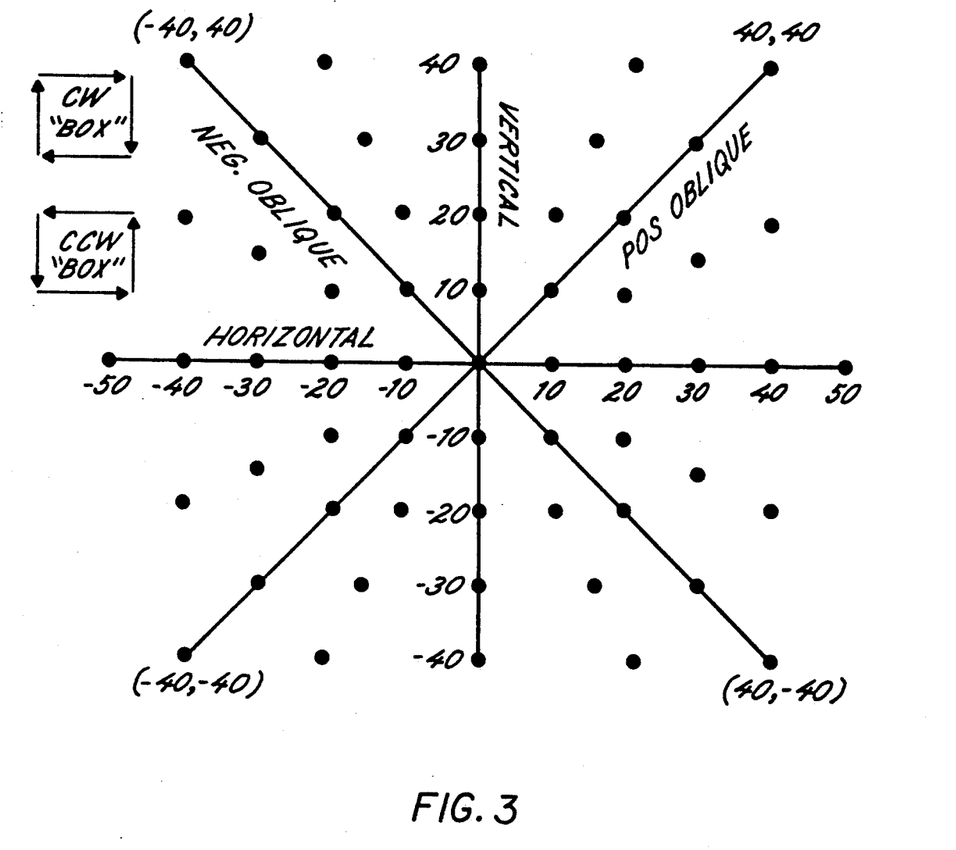
FIG. 3 illustrates a target means, which is comprised of a number of horizontal, vertical and oblique lines, which have landmarks that indicate specific angles, in a single plane or in the shape of a dome.
Figure 4A:
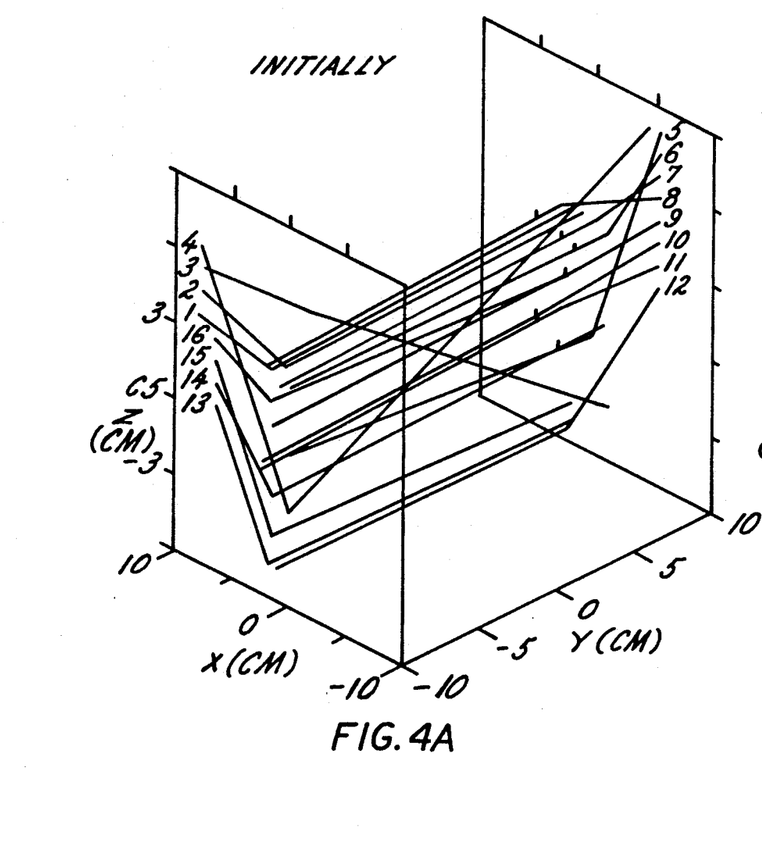
FIGS. 4a and 4b (after 6 weeks) illustrate 3-D plots of the derived finite axis of rotations for flexion-extension in 10° intervals for a normal patient.
Figure 4B:
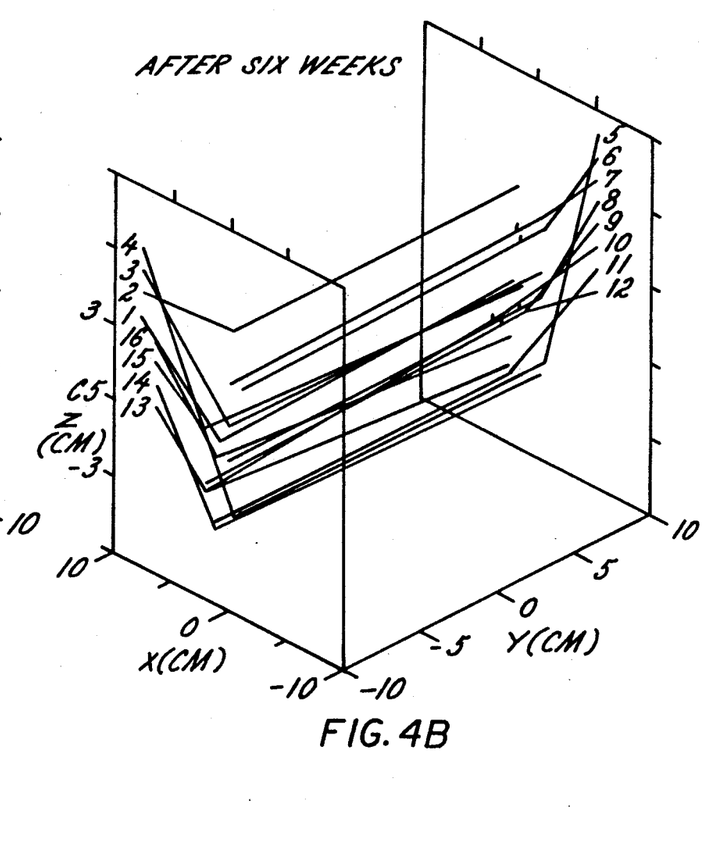

A normal patient, that is, one not afflicted with a whiplash injury, was tested for 3-D head movement, using the apparatus and method described heretofore. The patient's flexion-extension (vertical movement) was measured at 10° intervals over 40°. The patient was tested using the target means illustrated in FIG. 3 and the five target sequences described above. The screw axis for the vertical and horizontal movement were then calculated and plotted. The finite axis of rotation (defined by the screw axis parameters) is plotted, expressed in centimeters, relative to the fifth cervical vertebra (C5) as illustrated in FIG. 4a. The patient was then retested after six weeks (FIG. 4b) to determine the consistency of the movements of the patient over that time interval.

It can be seen from this data that the screw axis parameters of a normal patient vary smoothly in location and orientation. That smoothness in location and orientation of the movement was to be expected for a normal patient. In fact, the average (n=9) finite axis crossing for the entire normal population during 10° interval vertical movements was found to vary smoothly between the third cervical and first thoracic vertebrae. This example demonstrates the efficacy of the method and apparatus of the present invention to provide both the screw axis parameters of the head's movement and the mathematical values of such movement, the latter of which provide a complete description of the character of that movement. Accordingly, the method and apparatus of the present invention allow, for the first time, both the calculation of the screw-axis parameters of the head-neck system and a mathematical analysis of that movement for diagnostic and prognostic evaluation.

EXAMPLE II

Figure 5A:
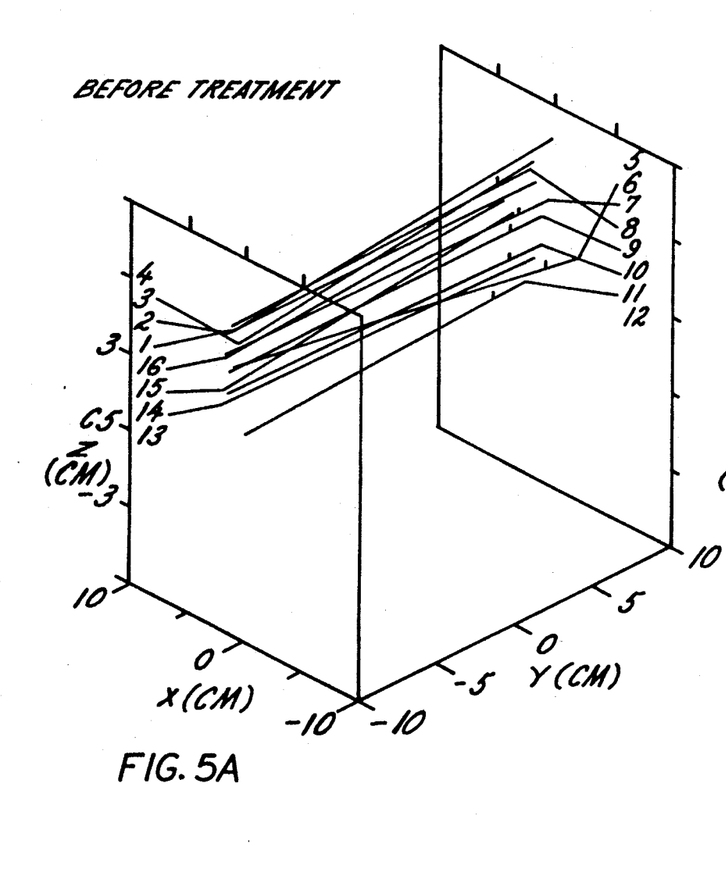
FIGS. 5a and 5b (after 6 weeks) illustrate 3-D plots of the derived finite axis of rotations for flexion-extension in 10° intervals for a person afflicted with a whiplash injury.
Figure 5B:
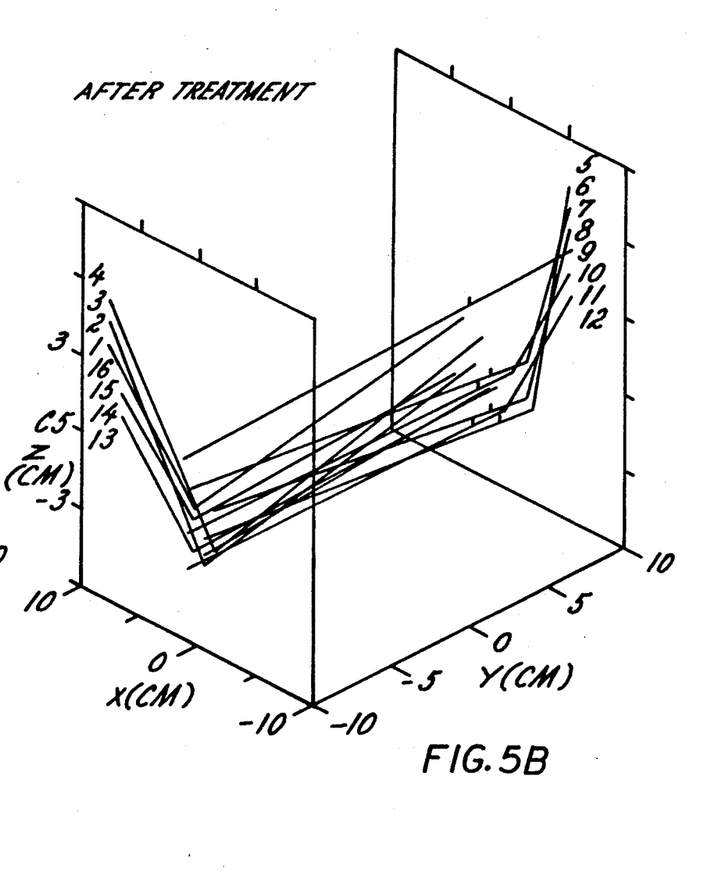

A patient afflicted with whiplash injury was tested for 3-D head movement in the same manner that the normal patient of Example I was tested. The patient's flexion-extension was measured at 10° intervals over 30°. The finite axis of rotation (defined by the screw axis parameters) for flexion-extension was then calculated and plotted for the patient as illustrated in FIG. 5. These screw axis parameters were plotted in different planes, expressed in centimeters, relative to the fifth cervical vertebra (C5). The patient was then retested six weeks later (FIG. 5b) after undergoing treatment for the whiplash injury.

It can be seen that for the patient with whiplash injury the screw axis location on the z-plane differs from that of the normal population. Before treatment, the patient tends to make all rotations about the upper cervical vertebrae (median axis approximately at the third cervical level), which may indicate problems in the lower neck region. After six weeks of treatment, the finite axis location on the z axis has shifted toward a more normal distribution, with the median axis located at approximately the fifth cervical vertebra.

We claim:

1. A non-invasive 3-D method for determining the kinematic function of the cervical spine of a human patient, comprising the steps of:
    a. positioning recordable, detectable marker means onto the head of the patient;
    b. using a target or instructional means to guide the patient through spatial head movements;
    c. recording the positions of said marker means as the patient moves his head in response to said target or instructional means;
    d. processing the recorded positions of the marker means by a 3-D analysis means to yield 3-D information of the marker means;
    e. processing the 3-D information of the marker means by a mathematical rigid body analysis means to derive screw axis parameters of the patient's head which define a 3-D instantaneous rotation of the patient's head and, optionally, a finite axis of rotation of the patient's head;
    f. using the axis of rotation of said patient's head as a measure of cervical kinematic function during head movements; and
    g. comparing the derived head axis of rotation for said patient either with a head axis of rotation for predetermined, standardized data to ascertain any discrepancy or with a previously derived head axis of rotation for said patient to identify changes.

2. A non-invasive 3-D method for determining the kinematic function of the cervical spine of a human patient, comprising the steps of:
    a. positioning recordable, detectable marker means onto the head of a patient;
    b. using a target or instructional means to guide the patient through spatial head movements;
    c. recording the positions of said marker means as the patient moves his head in response to the target or instructional means;
    d. storing the recorded positions of the marker means for processing to derive a 3-D instantaneous and-/or finite axis of rotation of the patient's head.
    e. processing the stored, recorded positions of the marker means by a mathematical rigid body analysis means to derive screw axis parameters of the patient's head which defines a 3-D instantaneous rotation of the patient's head and, optionally, a finite axis of rotation of the patient's head;
    f. using the axis of rotation of said patient's head as a measure of cervical kinematic function during head movements; and
    g. comparing the derived head axis of rotation for said patient either with a head axis of rotation for predetermined, standardized data to ascertain any discrepancy of with a previously derived head axis of rotation for said patient to identify changes.

* * * * *